United States Patent [19]

Bhise

[11] 4,400,559
[45] Aug. 23, 1983

[54] PROCESS FOR PREPARING ETHYLENE GLYCOL

[75] Inventor: Vijay S. Bhise, Bloomfield, N.J.

[73] Assignee: The Halcon SD Group, Inc., New York, N.Y.

[21] Appl. No.: 388,395

[22] Filed: Jun. 14, 1982

[51] Int. Cl.³ .............................................. C07C 31/20
[52] U.S. Cl. .................................. 568/858; 549/230; 549/513; 203/49; 260/463
[58] Field of Search ........................................ 568/858

[56] References Cited

U.S. PATENT DOCUMENTS 4,117,250 9/1978 Foster et al. .................... 568/858
4,237,324 12/1980 Rainer et al. .................... 568/858
4,283,580 8/1981 Odanaka et al. ................. 568/858

FOREIGN PATENT DOCUMENTS 267618 7/1970 U.S.S.R. ............................ 568/858

OTHER PUBLICATIONS

Peppel, "Industrial and Engineering Chemistry", vol. 50, No. 5 (May 1958), pp. 767–770.
U.S. Ser. No. 284,153, filed 7/17/81, Bhise, et al.
U.S. Ser. No. 321,966, filed 11/16/81, Bhise, et al.
U.S. Ser. No. 326,447, filed 12/2/81, Harvey Primary Examiner—J. E. Evans
Attorney, Agent, or Firm—William C. Long; Riggs T. Stewart; Harold N. Wells

[57] ABSTRACT

Ethylene glycol is prepared by a process in which ethylene oxide is extracted from an aqueous solution with near-critical or super-critical carbon dioxide. Thereafter an ethylene oxide—carbon dioxide—water mixture is contacted with a catalyst to form ethylene carbonate, which is then hydrolyzed to ethylene glycol in the presence of the same catalyst. The ethylene glycol is separated as product and the carbon dioxide and the catalyst are recycled.

9 Claims, 2 Drawing Figures

PROCESS FOR PREPARING ETHYLENE GLYCOL

PRIOR ART

The invention relates to the preparation of ethylene glycol from ethylene oxide. More particularly, the invention relates to a multi-step process wherein ethylene oxide is first converted to ethylene carbonate and thereafter the ethylene carbonate is hydrolyzed to ethylene glycol.

The process of the invention includes the extraction of ethylene oxide by (near) super-critical carbon dioxide as disclosed in U.S. patent applications Ser. No. 284,153 filed July 17, 1981 and Ser. No. 321,966 filed Nov. 16, 1981, the contents of which are incorporated by reference herein. Further, the process includes the reaction of ethylene oxide with carbon dioxide to form ethylene carbonate disclosed in U.S. patent application Ser. No. 326,447 filed Dec. 2, 1981 and also incorporated by reference herein.

The process of the invention combines the two processes just mentioned with the hydrolysis of ethylene carbonate to ethylene glycol to create an integrated process for producing ethylene glycol efficiently from an aqueous solution of ethylene oxide, such as those produced from the oxidation of ethylene. A synergistic combination is achieved. Formation of ethylene carbonate is particularly efficient when ethylene oxide has been extracted by carbon dioxide, since the combined stream can be used directly (or with intermediate partial separation of carbon dioxide) as feed to an ethylene carbonate reactor, even though it contains a small amount of water. The ethylene carbonate product from such a reaction can be hydrolyzed more efficiently to mono ethylene glycol than can ethylene oxide, which yields more of the higher glycols. Also, the catalyst used for carbonation is employed also for hydrolysis.

SUMMARY OF THE INVENTION

Ethylene glycol is prepared by a process comprising the steps of:
(a) extracting ethylene oxide from an aqueous solution with carbon dioxide at near-critical or super-critical conditions;
(b) contacting the ethylene oxide-rich carbon dioxide with a carbonation catalyst and reacting in the presence of a minor amount of absorbed water to form ethylene carbonate;
(c) adding water to the catalyst-containing ethylene carbonate-rich stream and hydrolyzing the ethylene carbonate in the presence of the carbonation catalyst to form ethylene glycol and carbon dioxide;
(d) flashing off carbon dioxide from the ethylene glycol-containing stream and returning the carbon dioxide to the (near) super-critical extraction step;
(e) separating the product ethylene glycol from the flashed stream of (d), and;
(f) recovering and recycling the catalyst to the carbonation reaction.

The bulk of the excess carbon dioxide used to absorb ethylene oxide preferably is removed before the carbonation step, but may be separated after carbonation, if desired.

The extraction of ethylene oxide may be carried out at a pressure of about 35–300 kg/cm$^2$ gauge and a temperature of about 0°–100° C.

The carbonation reaction may be carried out at a temperature of about 20°–90° C., selected to minimize the formation of ethylene glycol until the hydrolysis step, despite the presence of water absorbed during the extraction step. The catalyst employed may be at least one selected from the group consisting of organic quaternary ammonium halides, organic quaternary phosphonium halides, organic sulfonium halides, and organic antimony halides and will be used in a molar ratio catalyst to ethylene oxide of about 0.01 to 0.15.

The hydrolysis of ethylene carbonate to ethylene glycol may be carred out at about 90°–200° C. and with a molar ratio of water to ethylene carbonate of about 1–100, preferably about 1.1–20, especially 1.1–2.5. A higher percentage of mono ethylene glycol is produced than when ethylene oxide is hydrolyzed directly.

After hydrolysis of ethylene carbonate to ethylene glycol, the product glycols (mono and diethylene glycols) may be separated from higher-boiling by-products and the carbonation catalyst by successive distillation steps.

DESCRIPTION OF THE PREFERRED EMBODIMENTS

Ethylene oxide is commonly produced by the vapor phase oxidation of ethylene with molecular oxygen. The ethylene is passed over a supported silver catalyst along with oxygen and various inert ballast gases. The reaction has been extensively discussed in the art. For a brief description of the process, reference may be made to co-pending application Ser. No. 284,153. It is typical in such processes that the effluent from the ethylene oxide is scrubbed with a recirculating aqueous solution to produce a relatively dilute ethylene oxide solution, while the residual gases are recirculated to the reactor after impurities and by-products have been separated. The aqueous solution contains up to about 10 mol % ethylene oxide, along with minor amounts of by-products. In the conventional process, this aqueous solution is further purified and the ethylene oxide separated for use as such or for hydrolysis to ethylene glycol. It has been found that the ethylene oxide may be recovered selectively from the aqueous solution by contact with carbon dioxide under near-critical or super-critical conditions. For the present discussion, "near critical" refers to reduced temperatures in the range of about 0.6–1 and "super-critical" to reduced temperatures in the range of about 1–3. However, these ranges are not intended to limit the scope of the invention, but are primarily given for purposes of illustration.

Figure 1:
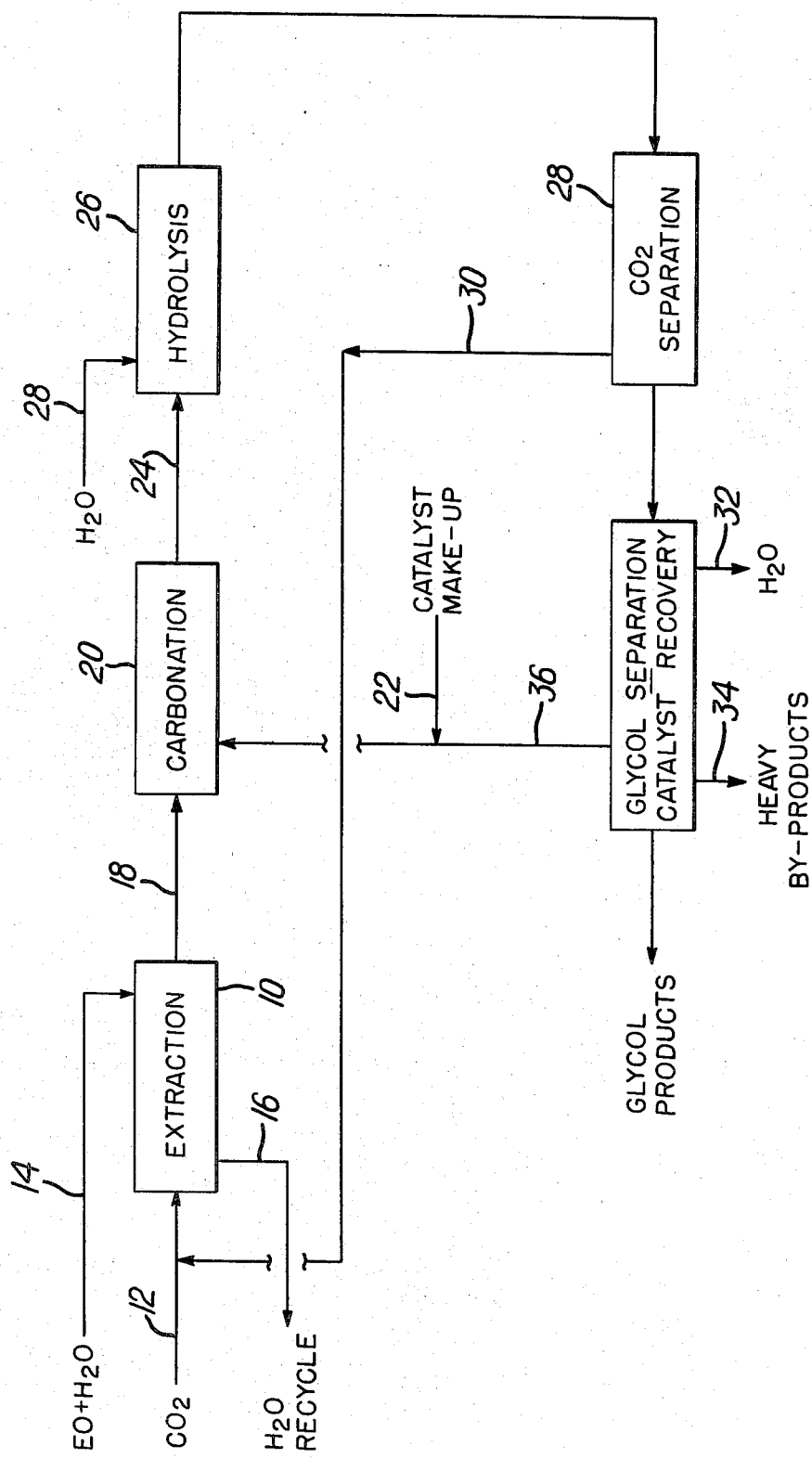
FIG. 1 is a block diagram showing the process of the invention.

As shown in FIG. 1, an extraction (10) may be carried out in which carbon dioxide (12) at high pressure and relatively low temperatures is used to extract ethylene oxide from an aqueous solution (14), producing an ethylene oxide-lean aqueous solution (16) which is recycled to the absorber (not shown). The extraction generally would be carried out at temperatures in the range of about 0°–100° C. and at pressures in the range of about 35–300 kg/cm$^2$ gauge.

The carbon dioxide, now rich in ethylene oxide, is especially suited as a feed (18) to carbonation step (20) where in the presence of water and a suitable carbonation catalyst (22), ethylene oxide, and carbon dioxide are reacted to form ethylene carbonate. The reaction may be carried out in the presence of a number of catalysts as disclosed in previously mentioned co-pending application Ser. No. 326,447, which generally include at least one member of the group consisting of organic quaternary ammonium halides, organic quaternary phosphonium halides, organic sulfonium halides, and organic antimony halides. The ethylene oxide-rich carbon dioxide 18 may be supplied directly to the carbonation reaction 20 or, alternatively, the bulk of the carbon dioxide may be flashed off leaving a fluid containing ample carbon dioxide to react with the ethylene oxide present. The carbonation reaction is carried out at a temperature in the range of about 20°–90° C. and with a mol ratio of catalyst to ethylene oxide of about 0.01–0.15.

Ethylene carbonate could be recovered following the carbonation reaction (20) as desired. According to the process of the present invention, the effluent (24) from the carbonation reaction (20) is supplied, with or without a partial removal of excess carbon dioxide, directly to a hydrolysis step (26) where, with the addition of water (28) and in the presence of the catalyst used for carbonation (22), hydrolysis is carried out at temperatures of about 90°–200° C. and with a mol ratio of water to ethylene carbonate of about 1–100, preferably 1.1–20, especially 1.1–2.5. As a result of this hydrolysis reaction, the ethylene carbonate is converted to monoethylene glycol with minor amounts of diethylene glycol and heavier by-products. Carbon dioxide produced in the hydrolysis reaction (26) is separated (28) for return (30) to the super-critical extraction step (10). Following this, the glycols are separated and purified by distillation from excess water (32) and heavy by-products (34), and the catalyst is separated for recycle (36) to the carbonation and hydrolysis reactions.

Figure 2:
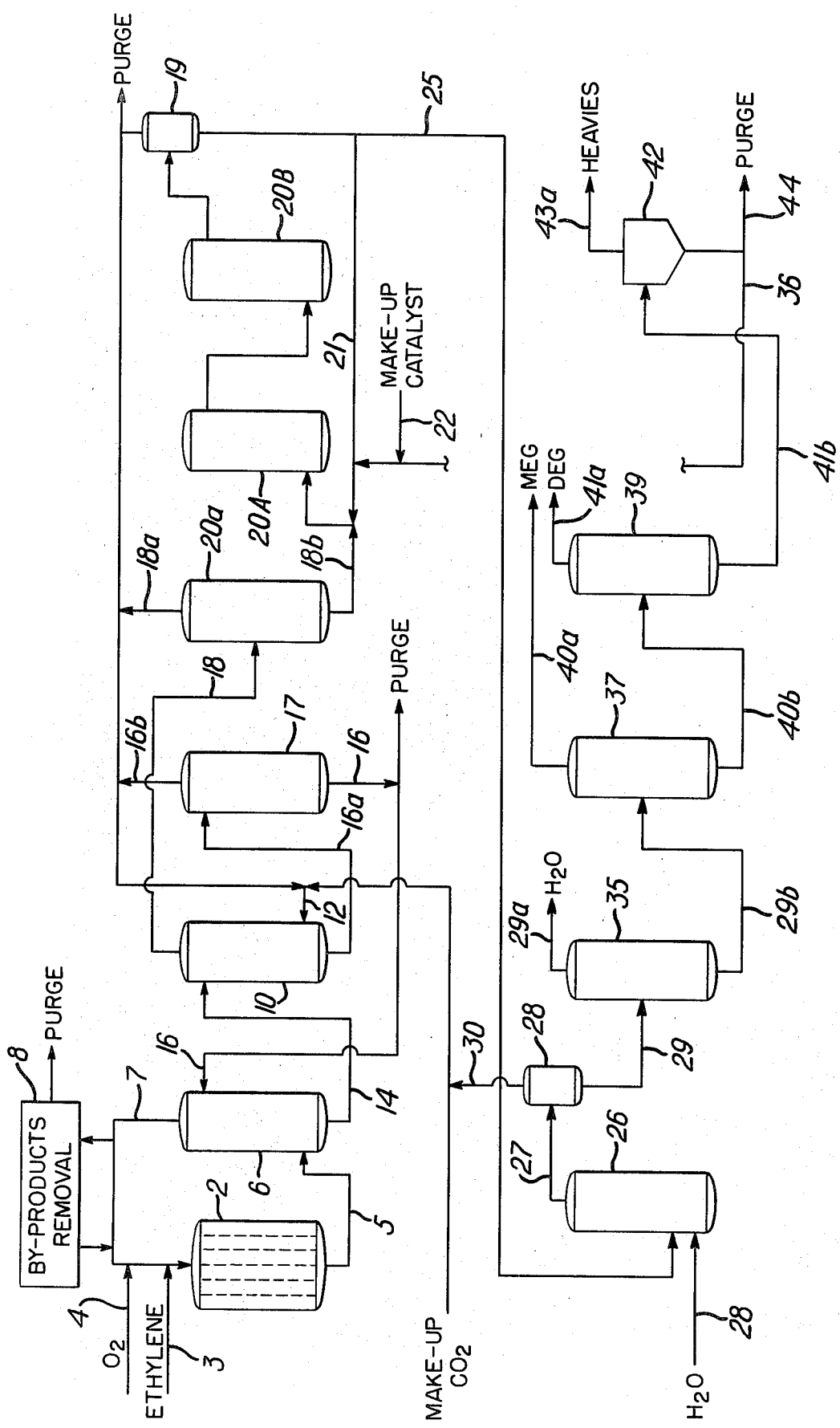
FIG. 2 is a simplified flowsheet illustrating a preferred embodiment.

A simplified flowsheet is provided in FIG. 2 to illustrate one practical application of the process of the invention. The reaction by which ethylene oxide is formed is shown briefly to include a reactor (2) wherein ethylene (3) is reacted with molecular oxygen (4) over a supported silver catalyst. The reactor effluent (5) is scrubbed with a circulating aqueous solution (16) for removal of the ethylene oxide in conventional scrubbing equipment (6), such as towers provided with vapor-liquid contacting trays and the like. The residual gases (7) are recirculated following the removal (8) of carbon dioxide and other by-products. The aqueous stream (14) containing ethylene oxide which is the principal feedstock for the process of the invention contains up to about 10 mol % ethylene oxide in water, along with minor amounts of by-products and unreacted materials from the ethylene oxide reactor, principally ethylene and carbon dioxide plus monoethylene glycol, which accumulates in the scrubbing system. This aqueous solution is fed to an extraction column (10) where it passes countercurrently to a stream of (near) super-critical carbon dioxide (12) under conditions selected to extract substantially all of the ethylene oxide present. The equipment could be any suitable contacting device known to those skilled in the art, a tower containing trays or packed beds being preferred. The stripped aqueous solution (16a) is passed to a flash vessel (17) operating at lower pressure to remove carbon dioxide absorbed in the water. The carbon dioxide-free water (16) then may be returned to the ethylene oxide scrubber for reuse. The carbon dioxide (16b) removed in the flash vessel joins other carbon dioxide and returns to the extraction column for reuse. Compression of these carbon dioxide streams will be necessary, but is not shown in this simplified figure. The ethylene oxide-rich carbon dioxide (18) is passed to the carbon dioxide separation column (20a) where, operating at slightly lower pressures, the bulk of the carbon dioxide (18a) is separated from the ethylene oxide for recycle to the extraction column (10). This flash step may be omitted if desired and the ethylene oxide-rich carbon dioxide fed directly to the carbonation reactors 20 A & B. It is considered economically advantageous, however, to remove the bulk of the carbon dioxide in order to reduce the size of equipment required for carbonation of the ethylene oxide. Since the effluent from the (near) super-critical extraction will typically contain about 0.5–30 mol % ethylene oxide, the balance being mainly carbon dioxide, the corresponding ratio in the feed (18b) to the carbonation reactors (20 A & B) may be between that required for the (near) super-critical extraction to near the theoretical 1:1 ratio for the carbonation reaction. Typically, however, this stream will have a mol ratio of ethylene oxide to carbon dioxide of about 0.2–1.

This mixture is fed along with one or more of the previously mentioned catalysts, preferably methyl triphenyl phosphonium iodide, to the carbonation reactors (20 A & B) in which ethylene carbonate will be formed at temperatures between about 20°–90° C. and pressures which range from about 3–100 kg/cm$^2$ gauge. Under these conditions formation of glycol is minimized even though some water is present. In order to assure good contacting of the catalyst with the reacting compounds, the carbonation reactors may contain mixing devices which limit backmixing and increase conversion to ethylene carbonate. Preferably, reactors simulating plug flow will be used. The reaction may take place in two successive reactors as shown with recirculation (21) in order to provide sufficient residence time for completion of the reaction, for example about 1 to 5 hours. Alternatively, any combination of reactors which simulate stirred tanks or plug flow maybe used. By flashing (19) the effluent from the reactors at a lower pressure, a minor amount of aldehydic impurities will be removed, which will entail a small loss of ethylene oxide and carbon dioxide from the system.

The products of the carbonation reaction, including the carbonation catalyst, then are passed directly to the hydrolysis reactor (26) where sufficient water (28) is added to carry out the complete hydrolysis of ethylene carbonate to ethylene glycols, primarily mono ethylene glycol. Typically, this will require a mol ratio of water to ethylene carbonate of between 1.1–20, preferably about 1.1–2.5. The reaction will be carried out at temperatures of about 90°–200° C. and at pressures of about 3–100 kg/cm$^2$ gauge. As with the carbonation reactors (20 A & B), the hydrolysis reactor (26) will require sufficient volume in order for the reaction to be completed and adequate contacting to ensure efficiency, for example, about 0.5 to 4 hours. The vessel(s) may be any combination of reactors which simulate stirred tanks or plug flow. Hydrolysis of ethylene carbonate to ethylene glycol releases carbon dioxide from the ethylene carbonate. This carbon dioxide is removed by flashing the product stream (27) in a vessel (28) at a lower pressure. The carbon dioxide gas may be recycled (20) for further use in (near) super-critical extraction of ethylene oxide (10).

After this flash, the liquid stream (29) consists primarily of water, monoethylene glycol, heavy impurities such as polyethylene glycols, catalyst and small amounts of diethylene glycol. This stream may be processed for recovery of the desired products and removal of by-products as shown by a series of evaporation and distillation steps. Stream (29) is first fed into a distillation column (35) operating at sub-atmospheric pressure of about 10 to 500 mm Hg absolute in which excess water is removed as an overhead stream (29a). This may be reused in the hydrolysis reaction or disposed of if desired. The bottoms (29b) from the column (35) contain the principal product, i.e. monoethylene glycol, heavy by-products, catalyst, and minor amounts of diethylene glycol. This stream is then fed to a second distillation column (37) where the monoethylene glycol is taken over as a product (40a), while the heavier materials are removed as a bottoms product (40b). This bottoms product (40b) is fed to a third distillation column (39) where diethylene glycol is taken overhead (41a), while the heavier by products (41b) are removed as bottoms and fed to an evaporator (42) where they are removed as a vapor (43a) and the catalyst is removed as a liquid stream (36) for return to the carbonation reactors (20 A & B). The heavy by-products may be disposed of, if desired. A minor purge (44) typically will be removed from the catalyst stream in order to eliminate any heavy materials not vaporized to avoid excess build-up in the recirculating catalyst stream.

The following example provides details of a preferred embodiment according to the flowsheet of FIG. 2.

EXAMPLE 1

The ethylene oxide reactor (2) operating at a temperature of about 240° C. and 17 kg/cm$^2$ gauge forms ethylene oxide by reacting ethylene and molecular oxygen over a supported silver catalyst. The reactor effluent (5) is cooled and scrubbed in column (6) with 98,300 mol/hr of a recirculating stream (16) containing 99.8% H$_2$O, and 0.14% monoethylene glycol. The resulting 100,000 mols/hr of solution 14 contains 948 mols/hr of ethylene oxide, small amounts of dissolved gases, such as ethylene and carbon dioxide, 140 mols/hr of monoethylene glycol and small amounts of other materials derived from the ethylene oxide reactor effluent stream (5). Stream (14) contacts 41,700 mols/hr of carbon dioxide (12) at 45° C. and 85 kg/cm$^2$ gauge in a sieve-tray extractor (10). The stripped aqueous stream (16a) of 101,960 mols/hr contains 2.9% CO$_2$ and 0.14% monoethylene glycol. This stream (16a) is stripped of 99% of the carbon dioxide it contains in flash vessel (17). This carbon dioxide is compressed and returned to extractor (10). The stripped solution is returned (16) to absorber (6). The ethylene oxide-rich carbon dioxide stream (18) contains substantially all of the ethylene oxide in stream (14) along with equilibrium amounts of materials derived from the ethylene oxide reactor effluent (5). Such materials are allowed to build up to a desired level and maintained by purging a portion of the recirculating stream (16). The carbon dioxide stream (18) is reduced in pressure to about 60–65 kg/cm$^2$ gauge to remove the bulk of the carbon dioxide and light impurities for recycle to the extractor (10). The liquid product (18b) of 3012 mols/hr contains 31.5% ethylene oxide, 0.3% water, and trace impurities. It will be understood that the ratio of carbon dioxide to ethylene oxide can be adjusted as desired to provide a mixture suitable for the formation of ethylene carbonate. The bottoms from the CO$_2$ separator (20a) is combined with 1970 mols/hr of recirculating stream 21, which is principally ethylene carbonate, but contains about 3 mol % catalyst (methyl triphenyl phosphonium iodide) and about 28 mol % of heavy by-products, as determined by amount purged. It will be understood that the amount of heavy by-products made in the hydrolysis reactor, principally higher glycols, will be rather small. However, they may be allowed to accumulate to serve as a carrier for the catalyst recirculation.

The carbonation reactors (20 A and B) operate at 63 kg/cm$^2$ gauge and 90° C. with a residence time of 1–5 hours to convert 99.5 of the ethylene oxide to ethylene carbonate. After the flash in vessel (19), the net product stream (25), which removes excess carbon dioxide for recirculation to the extractor, contains about 68.5 mol % ethylene carbonate, 27.5 mol % heavy by-products, and 3.2 mol % catalyst, plus minor amounts of water and glycols. To this stream (25) is added 1620 mols/hr of water (a ratio of water/carbonate of 1.7/1) and the hydrolysis carried out in reactor (26) at a temperature of about 150° C. and a pressure of 63 kg/cm$^2$ gauge. All of the ethylene carbonate fed is converted, with 98.9% going to monoethylene glycol and the remainder to diethylene glycol and higher glycol by-products. A mol of carbon dioxide is released for each mol of ethylene carbonate converted. This is flashed off in vessel (28) for recycle to the extractor (10). The liquid stream (29) from the flash vessel contains about 930 mols/hr monoethylene glycol, 2.8 mols/hr diethylene glycol, 695 mols/hr water, 380 mols/hr heavy by-products, and 44 mols/hr catalyst. Substantially all of the water is removed in distillation column (35) operating at about 300 mm Hg absolute pressure (bottom). The bottoms product (29b) contains the monoethylene glycol, diethylene glycol, heavy by-products, and catalyst, which is distilled in column (37) at about 85 mm Hg absolute pressure (bottom) to remove substantially all of the monoethylene glycol overhead (40a) as product. The bottoms product (40b) is distilled in column (39) at about 85 mm Hg absolute to separate diethylene glycol as an overhead product (41a). The bottoms stream (41b) contains essentially only heavy by-products and catalyst. The net make of heavy by-products, about 0.4–0.5 mols %, is evaporated (42) and the remaining by-products and catalyst are recycled to the carbonation reactors (20 A & B), after a small purge is taken (44). Catalyst lost in the reactions and separations is added via stream (22), intermittently or continually as desired.

What is claimed is:

1. A process for the preparation of ethylene glycol from an aqueous solution of ethylene oxide comprising the steps of:
   (a) contacting said aqueous solution of ethylene oxide with sufficient carbon dioxide at near-critical or super-critical conditions to extract substantially all of the ethylene oxide into the carbon dioxide and forming an ethylene oxide-rich carbon dioxide phase containing a minor amount of water and an ethylene oxide-lean aqueous phase;
   (b) contacting said ethylene oxide-rich carbon dioxide phase of (a) with a carbonation catalyst under carbonation conditions to form an ethylene carbonate-rich carbon dioxide stream;
   (c) adding water to the catalyst-containing ethylene carbonate-rich stream of (b) and hydrolyzing said ethylene carbonate to ethylene glycol and carbon dioxide;

(d) flashing off from the ethylene glycol-containing stream of (c) the carbon dioxide formed in the hydrolysis and returning said carbon dioxide to the (near) super-critical extraction of (a);

(e) separating the ethylene glycol from the flashed stream of (d); and (f) recovering and recycling to the carbonation reaction the catalyst added in (b).

2. The process of claim 1 further comprising the step of separating the ethylene oxide-rich carbon dioxide phase of (a) from said ethylene oxide-lean aqueous phase and flashing said separated carbon dioxide phase to a lower pressure, thereby vaporizing a portion of the carbon dioxide and separating a liquid stream containing a lower ratio of carbon dioxide to ethylene oxide which is supplied as the ethylene oxide-rich carbon dioxide phase to the carbonation reaction of (b).

3. The process of claim 1 wherein said carbonation of (b) is carried out at a temperature of 20°–90° C. and with a molar ratio of catalyst to ethylene oxide about 0.01 to 0.15, said catalyst being at least one of the group consisting of organic quaternary ammonium halides, organic quaternary phosphonium halides, organic sulfonium halides, and organic antimony halides.

4. The process of claim 1 wherein said extraction of (a) is carried out at a pressure of about 35–300 kg/cm$^2$ gauge and a temperature of about 0°–100° C.

5. The process of claim 1 wherein said hydrolysis of (c) is carried out at about 90°–200° C. and with a molar ratio of water to ethylene carbonate of about 1–100.

6. The process of claim 1 wherein said flashed stream of (d) is distilled in a first column to remove water as an overhead product and separating glycols, heavy by-products, and catalyst as a bottoms product.

7. The process of claim 6 wherein said bottoms product is distilled in a second column to separate monoethylene glycol as an overhead product and diethylene glycol, heavy by-products, and catalyst as a bottoms product.

8. The process of claim 7 wherein said bottoms product of the second column is distilled in a third column to separate diethylene glycol as an overhead product and heavy by-products and catalyst as a bottoms product.

9. The process of claim 8 wherein said bottoms product of said third column is evaporated to remove heavy by-products as vapor and separating said catalyst for recycle to step (b).

* * * * *

UNITED STATES PATENT AND TRADEMARK OFFICE
CERTIFICATE OF CORRECTION

PATENT NO. : 4,400,559
DATED : August 23, 1983
INVENTOR(S) : Vijay S. Bhise

It is certified that error appears in the above-identified patent and that said Letters Patent are hereby corrected as shown below:

Column 2, line 12: Change "carred" to -- carried --;

Column 6, line 13: Change "99.5" to -- 99.5% --.

Signed and Sealed this

Nineteenth Day of March 1985

[SEAL]

Attest:

DONALD J. QUIGG

Attesting Officer

Acting Commissioner of Patents and Trademarks